United States Patent [19]

Rose

[11] 4,104,020
[45] Aug. 1, 1978

[54] HAIR DYE COMPOSITIONS CONTAINING 4,7-DIAMINOINDAZOLES

[75] Inventor: David Rose, Hilden, Germany

[73] Assignee: Henkel Kommanditgesellschaft Auf Aktien, Düsseldorf-Holthausen, Germany

[21] Appl. No.: 695,454

[22] Filed: Jun. 14, 1976

[30] Foreign Application Priority Data

Jun. 21, 1975 [DE] Fed. Rep. of Germany ....... 2527791

[51] Int. Cl.$^2$ ............................................. A61K 7/13
[52] U.S. Cl. ........................................... 8/10.2; 8/10; 8/10.1; 8/11; 8/32; 548/371
[58] Field of Search ............... 260/310 C; 8/10.2, 11, 8/32, 10, 10.1

[56] References Cited

U.S. PATENT DOCUMENTS

| | | | |
|---|---|---|---|
| 2,315,220 | 3/1943 | Petitcolas et al. | 260/310 C |
| 3,133,081 | 5/1964 | Lafferty et al. | 260/310 C |
| 3,176,020 | 3/1965 | Sureau et al. | 260/310 C |
| 3,711,506 | 1/1973 | Wagner et al. | 260/310 C |
| 3,766,207 | 10/1973 | Minieri | 260/310 C |
| 3,849,064 | 11/1974 | Wiskott | 8/10.2 |

OTHER PUBLICATIONS

Chemical Abstracts, vol. 50, columns 4917–4919, (1956).

*Primary Examiner*—Albert T. Meyers
*Assistant Examiner*—Vera C. Clarke
*Attorney, Agent, or Firm*—Hammond & Littell

[57] ABSTRACT

Dyestuffs of the oxidizable developer-coupler type wherein the developer is a novel 4,7-diaminoindazole of the formula:

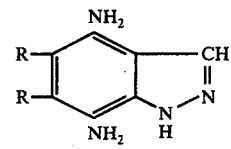

wherein one of the R's represents $C_{1-4}$ alkyl and the other R represents a substitutent selected from the group consisting of $C_{1-4}$ alkyl and H (and the water-soluble salts thereof) are very satisfactory for coloring hair. They are readily oxidized by atmospheric oxygen at room temperature without a catalyst, and they provide intense, bright, and fast dyeings in a short time. They are applied in conventional manner from aqueous medium.

21 Claims, No Drawings

HAIR DYE COMPOSITIONS CONTAINING 4,7-DIAMINOINDAZOLES

FIELD OF THE INVENTION

The present invention relates to novel oxidizable developer-coupler dyestuff combinations for the dyeing of hair wherein the developer component comprises a 4,7-diaminoindazole derivative. The invention includes the developer-coupler combinations themselves, preparations for the dyeing of hair wherein the dye component includes the aforesaid novel developer-coupler combinations, and the processes involved. The invention further includes the novel 4,7-diaminoindazole derivatives themselves.

BACKGROUND OF THE INVENTION

Of great importance for the dyeing of hair are the so-called oxidation dyestuffs because of the intense and very fast dyes which they provide. These dyes are formed by the oxidative coupling of a developer component with a coupling component. The developers customarily used are nitrogenous bases such as p-phenylenediamine derivatives, diaminopyridines, 4-aminopyrazolone derivatives, or heterocyclic hydrazones. Useful as so-called coupling components are m-phenylenediamine derivatives, phenols, naphthols, resorcinol derivatives and pyrazolones. Compositions of this type are disclosed in application Ser. No. 526,232 filed on Nov. 22, 1974, by Rose et al., now U.S. Pat. No. 4,003,699, Jan. 18, 1977.

Good oxidation dyestuff components for the dyeing of hair should fulfill the following requirements.

They should develop the desired shades with sufficient intensity when oxidatively coupled with the respective developer component or coupling component, as the case may be. Furthermore, they have to possess an adequate capacity for being absorbed or adsorbed by human hair. In addition, they should be harmless from the toxicological and dermatological viewpoints.

It must form a tint of desirable hue of adequate intensity upon oxidative coupling with the opposite member of its pair. Furthermore, it must have an adequate to very good ability to be absorbed by human hair, and it should be harmless from the toxicological and dermatological viewpoints.

As developers, it is customary to use substituted or unsubstituted p-phenylenediamines for the purpose. However, this group of compounds has the disadvantage in many instances of causing skin sensitization and subsequent severe allergies in the persons to whom these compounds are applied. The developers which have been recently proposed for avoiding these dermatological disadvantages do not always give fully satisfactory technical results when applied.

OBJECTS OF THE INVENTION

An object of the invention is to provide usable hair dye compositions of the developer-coupler type which satisfy the above requirements.

A further object of the invention is to provide compositions of this type which, when oxidized, provide dyeings over a broad color range.

A still further object is to provide compositions of the type which can be applied to hair in a customary emulsion carrier at an alkaline pH, and which develop their color without need for pH adjustment.

Another object of the present invention is to provide an oxidation dyestuff combination of a coupling component and a developer component, which is based on water-soluble 4,7-diaminoindazole derivatives as the developer component.

THE INVENTION

It has now been found that hair dyestuffs based on oxidative developer-coupler components meet these objects when the developer component is a 4,7-diaminoindazole derivative of the formula:

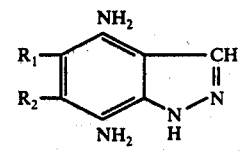

in which $R_1$ and $R_2$ represent an alkyl radical of 1 to 4 carbon atoms, the other radical being hydrogen if only one of the radicals is an alkyl radical, or an inorganic or organic salt thereof. More simply, the developer components can be (I) a compound represented by the formula:

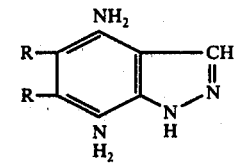

wherein one of the R's represents $C_{1-4}$ alkyl and H, and the other $C_1$-$C_4$ alkyl and (II) the water-soluble salts thereof.

The above 4,7-diaminoindazoles, when applied in conjunction with conventional couplers generally used for oxidation hair dyeing, provide varied and very intense dyeings and thus constitute a substantial enrichment of the art of oxidation hair dyeing. Furthermore, the dyeings are distinguished by very good fastness.

The 4,7-diaminoindazole-coupler dyestuffs of the present invention possess solubility in water and good storage stability, and their behavior is advantageous from a toxicological and dermatological viewpoint.

It has further been found that the following preparation is especially suitable for the dyeing of human hair, said preparation consisting essentially of:

(1) 0.2% to 5% by weight of a hair dyestuff as described above.
(2) 0.5% to 30% by weight of a non-cationic surfactant;
(3) 0.1% to 25% by weight of a thickener;
(4) 0% to 5% by weight of a direct dye for hair;
(5) 0% to 5% by weight of an oxidizing agent; and
(6) water.

The preparation preferably has a pH in the range of 8–10, the thickener is preferably a hydrophobic material, the preparation is an emulsion of cream viscosity, the preferred developer components are 4,7-diamino-5-methylindazole and 4,7-diamino-5-6-dimethylindazole, the preferred coupler component is guaiacol, the preferred surfactant is the sodium salt of the half ester of a $C_{12}$–$C_{18}$ fatty alcohol with sulfuric acid, and the preferred oxidizing agent is hydrogen peroxide.

We have further found that hair can be successfully dyed by contacting hair with the foregoing preparation at a temperature between 15° C. and 40° C. with access of air until at least part of the dyestuff in the preparation has oxidized and the hair has acquired the desired shade, and then washing the hair to remove the residue of the preparation. If desired, a synthetic oxidizing agent can be incorporated in the preparation before it is applied to the hair. Preferably the preparation, as applied has an alkaline pH.

The 4,7-diaminoindazole derivatives which are used as developer components according to the invention can be used either as such (i.e., in free base form) or in form of their water-soluble salts with non-toxic (i.e. dermatologically acceptable) inorganic or organic acids, such as hydrochloric acid, sulfuric acid, phosphoric acid, acetic acid, propionic acid, lactic acid or citric acid.

The aforesaid 4,7-diaminoindazole derivatives can be produced by generally known processes by catalytic hydrogenation of the corresponding 4,7-dinitroindazole derivatives. The 4,7-diaminoindazole derivatives used in accordance with the present invention have not hitherto been described in the literature.

4,7-Diaminoindazole derivatives suitable as the developer components of the dyestuffs of the present invention are, for example, 4,7-diamino-5-methylindazole, 4,7-diamino-5-ethylindazole, 4,7-diamino-5-propylindazole, 4,7-diamino-5-isopropylindazole, 4,7-diamino-5-butylindazole, 4,7-diamino-6-methylindazole, 4,7-diamino-6-ethylindazole, 4,7-diamino-6-propylindazole, 4,7-diamino-6-isopropylindazole, 4,7-diamino-6-butylindazole, 4,7-diamino-5,6-dimethylindazole, 4,7-diamino-5,6-diethylindazole, 4,7-diamino-5,6-dipropylindazole, 4,7-diamino-5,6-diisopropylindazole, 4,7-diamino-5,6-dibutylindazole, 4,7-diamino-5-methyl-6-ethylindazole, and 4,7-diamino-5-methyl-6-isopropylindazole.

Specific examples of preferred coupling components to be used for the hair dyes according to the invention are as follows:

α-Naphthol
o-Cresol
m-Cresol
2,6-Dimethylphenol
2,5-Dimethylphenol
3,4-Dimethylphenol
3,5-Dimethylphenol
Pyrocatechol
Pyrogallol
1,5-Dihydroxy naphthalene
1,7-Dihydroxy naphthalene
5-Amino-2-methylphenol
Hydroquinone
2,4-Diaminoanisole
m-Toluenediamine
4-Aminophenol
Resorcinol
Resorcinol monomethyl ether (3-methoxyphenol)
m-Phenylenediamine
3-Methyl-1-phenyl-5-pyrazolone
3-Amino-1-phenyl-5-pyrazolone
1-Phenyl-3,5-dione-pyrazolidine
7-(Dimethylamino)-4-hydroxy-1-methyl-2-quinolone
1-Amino-3-(acetacetylamino)-4-nitrobenzene
1-Amino-3-(cyanoacetylamino)-4-nitrobenzene In the hair dye preparations according to the invention, the developer and coupling components are present in substantially equimolecular proportions. Although an equimolar amount is preferred, it is possible to use more or less of either component in the molar range of 2:1 to 1:2.

It is not necessary for the developer and the coupling components to be single chemical entities. Instead, either or both may be mixtures of compounds suitable for the respective purposes. Thus the developer component can be a mixture of several 4,7-diaminoindazole derivatives suitable for use according to the invention, and the coupling component can also consist of a mixture of one or more of the above-named coupling components.

In addition, the hair dyeing preparations according to the invention can contain admixtures of other customary developer components and, if necessary, can also contain customary direct dyestuffs in case the latter are needed for obtaining certain shades. From 0% to 5% of direct dyestuffs may be present.

As in the case of other oxidation hair dyes, the oxidative coupling (i.e., the development of the color of the dye) can be effected by atmospheric oxygen. However, it is preferred to use a chemical oxidizing agent. Suitable oxidizing agents are hydrogen peroxide or its addition products with urea, melamine and sodium borate, as well as mixtures of such hydrogen peroxide addition products with potassium peroxydisulfate.

When the 4,7-diaminoindazole derivatives according to the invention are used as developer components, they have the advantage of providing highly satisfactory hair dyeing results with atmospheric oxygen. Thus, damage to the hair by the oxidizing agent generally used for oxidative coupling can be avoided. But if bleaching and dyeing of the hair are simultaneously desired, then the concurrent use of a chemical oxidizing agent is necessary.

Alternatively, the joint use of another coupler component can be dispensed with in special cases, since the 4,7-diaminoindazole derivatives are able, under self-condensation with at least one further mol of the 4,7-diaminoindazole derivative which acts as a coupler component in this case, to provide hair dyes with attractive tints under the oxidative effect of air or oxidation agents.

For use, the hair dye combinations according to the invention are incorporated into a suitable aqueous cosmetic preparation such as a cream, emulsion, gel or simple solution, and immediately before the preparation is applied to the hair, one of the above-named oxidizing agents is mixed therewith. The concentration of the developer-coupler combinations in the hair dyeing preparation is between 0.2% to 5% by weight, preferably from 1% to 3% by weight.

For the preparation of creams, emulsions or gels, the dye components, separately or as dry blend, are mixed with additional ingredients customarily used in such preparations. Such additional ingredients are, for example: wetting agents or emulsifiers of the anionic or nonionic type such as alkylbenzenesulfonates, fatty alcohol sulfates, alkylsulfonates, fatty acid alkanolamides, ethoxylated fatty alcohols; and thickeners, such as methyl cellulose, starch, higher fatty alcohols, paraffin oil, and higher fatty acids. Furthermore, perfumes and hair-conditioning and grooming agents, such as pantothenic acid and cholesterol may be included.

Effective amounts of the above-named additives are those customarily employed for this purpose. Effective amounts of wetting agents and emulsifiers range from 0.5% to 30% by weight, preferably from 1% to 15% by weight; and for thickeners, an effective amount ranges from 0.1% to 25% by weight, preferably from 1% to 15% by weight, based in each case on the total weight of the preparation. As a lower limit for the above additives, a zero percent lower limit is possible, if none of the additive is utilized.

The hair coloring preparations according to the invention can be applied in a weakly acid medium, a neutral medium or especially, in an alkaline medium, preferably at a pH of 8 to 10 regardless whether the medium is a solution, an emulsion, a cream, or a gel. These preparations are usually applied at a temperature in the range of 15° C. to 40° C., and are preferably applied at room temperature.

After the preparation has been allowed to remain in contact with the hair for about 30 minutes, the preparation is rinsed off and the hair is washed with a mild shampoo and dried.

Very strong and attractive colorings can be produced by application of the hair dye preparations of the present invention. The colors obtained have satisfactory fastness with respect to light, to washing and to rubbing, and excess dye is readily removed by application of a reducing agent.

The present invention is further illustrated by the examples which follow. These examples are the best modes contemplated by the invention, and are not to be construed in limitation thereof.

EXAMPLE I

The following illustrates the preparation of a novel 4,7-diaminoindazole derivative useful in the present invention.

(1) 4,7-Diamino-5-methylindazole.

(A) 4,7-Dinitro-5-methylindazole.

To 9.8 g. of 1,3-dimethyl-2,5-dinitro-4-aminobenzene dissolved in 450 ml. of glacial acetic acid was slowly added dropwise 24 ml. of 2N sodium nitrite solution, the temperature being maintained at 15° C. The resulting dark red solution was added dropwise to 250 ml. of boiling 2N sulphuric acid and the solution was boiled for twenty minutes under reflux. The solution was cooled and poured upon ice, and the precipitate which formed was drawn off. Yield: 3.7 g. of brown crystals; melting point 140° C. - 144° C. Analysis:

|  | %C | %H |
|---|---|---|
| Calculated | 43.25 | 2.72 |
| Found | 45.4 | 3.08 |

(B) 4,7-Diamino-5-methylindazole-1,5-sulfate.

3.35 g. of 4,7-dinitro-5-methylindazole were dissolved in 100 ml. of ethanol and hydrogenated at room temperature with 0.1 g. of catalyst (10% Pd on carbon). After absorption of hydrogen ceased, the product was filtered off from the catalyst and 40 ml. of 2N $H_2SO_4$ were added. The precipitate which formed was drawn off, washed with water and dried. Melting point > 250° C. Analysis:

|  | %C | %H | %N | %S |
|---|---|---|---|---|
| Calculated | 31.2 | 3.9 | 18.2 | 13.9 |
| Found | 33.2 | 4.1 | 18.2 | 13.7 |

(2.) 4,7-Diamino-5,6-dimethylindazole dihydrochloride monohydrate.

1.8 g. of 4,7-dinitro-5,6-dimethylindazole, prepared in accordance with the procedure of E. Nelting, Ber. 37, 2556 (1904), were hydrogenated at room temperature in 50 ml. of ethanol and 5 ml. of concentrated hydrochloric acid in the presence of 0.1 g. of catalyst (10% Pd on carbon). After the absorption of $H_2$ ceased, the product was filtered off from the catalyst and reduced. Brown crystals were obtained. Analysis:

|  | %C | %H | %Cl |
|---|---|---|---|
| Calculated | 40.3 | 5.6 | 26.5 |
| Found | 39.16 | 5.4 | 26.9 |

Infrared data ($cm^{-1}$): 1649, 1592, 1518, 1460, 1436, 1400, 1368, 1342, 1290, 1233 1210, 1168, 1090, 1010, 930, 860, 745, 650.

EXAMPLE II

The following illustrates hair dye preparations in accordance with the present invention, in the form of emulsions of cream viscosity.

0.01 mol of each of the respective 4,7-diaminoindazole derivatives and coupler substances listed in the following table were incorporated in an emulsion prepared by rapidly agitating a hot mixture of:
- 10 parts by weight of $C_{12}$–$C_{18}$ fatty alcohols.
- 10 parts by weight of the sodium salts of the half esters of sulfuric acid with $C_{12}$–$C_{18}$ fatty alcohols.
- 75 parts by weight of water. in a laboratory blender, homogenizing the product, and cooling the resulting emulsion. The pH value of the emulsion was then adjusted to 9.5 by addition of ammonia and the emulsion was made up to 100 parts by weight with water.

Oxidative coupling was effected either with atmospheric oxygen or with 1% hydrogen peroxide solution as the oxidation agent, 10 parts by weight of hydrogen peroxide solution being added to 100 parts by weight of the emulsion.

The creams (with and without oxidation agent) were applied to human hair which was 90% grey and which had not been specially pretreated, and in each instance the cream was left on the hair for 30 minutes with access of air, at which time the dyeing process was substantially complete. The hair was then washed with a conventional shampoo to remove the residue of the hair dyeing preparation, and the colors which formed are shown in Table I.

TABLE 1

| Run No. | Dye Components Developer | Coupler | Color of Hair After Oxidation by Atmospheric Oxygen | 1% $H_2O_2$ Solution |
|---|---|---|---|---|
| 1 | | 4,7-Diamino-5-methylindazole | Dark green | Dark green |
| 2 | | Resorcinol monomethyl-ether | Pale green | Pale green |
| 3 | | 1-Phenyl-3-amino-pyrazolone-5 | Brownish orange | Brownish orange |
| 4 | 4,7-Diamino-5-methylindazole | α-Naphthol | Dark green | Dark turquoise |
| 5 | | 2,4-Diaminoanisole | Dark blue | Dark blue |
| 6 | | m-Toluenediamine | Dark turquoise | Dark blue |

TABLE 1-continued

| Run No. | Dye Components Developer | Coupler | Color of Hair After Oxidation by Atmospheric Oxygen | 1% H$_2$O$_2$ Solution |
|---|---|---|---|---|
| 7 | | Resorcinol | Dark green | Pale green |
| 8 | | 4,7-Diamino-5,6-dimethyl-indazole | Yellowish brown | Olive brown |
| 9 | | m-Aminophenol | Olive | Olive |
| 10 | | α-Naphthol | Pale green | Pale green |
| 11 | 4,7-Diamino-5,6-dimethyl-indazole | o-Cresol | Olive brown | — |
| 12 | | 2,4-Diaminoanisole | Dark green | Pale green |
| 13 | | Resorcinol monomethyl-ether | Olive brown | Olive brown |
| 14 | | 5-Amino-2-methyl-phenol | Pale green | Pale green |

It can be seen from the above table that the development of the dyeing properties of the developer-coupler combination can be effected with atmospheric oxygen and that the process provides intense and attractive hues which are distinguished by satisfactory fastness with respect to light, washing and rubbing.

For purposes of comparison a series of dyeings was performed with aminoindazoles which had been disclosed in the literature. The dyeings were performed in the same manner as those shown in the above table, with the exception that 5,6-diaminoindazole and 6-aminoindazole were used in each instance instead of the 4,7-diaminoindazole derivatives used in accordance with the present invention. The results obtained are shown in Tables 2 and 3.

These tests show that both 5,6-diaminoindazole and 6-aminoindazole do not produce dyeings with air oxidation, and that only dull dyeings (greyish brown to brownish grey) are produced when synthetic oxidation agents are used.

The 4,7-diaminoindazole derivatives of the present invention have the important advantage that they provide the desired dyeings by air oxidation (i.e., without need for a chemical oxidation agent) and moreover, they provide far more intense and more varied colors.

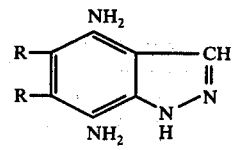

wherein one of said R's represents C$_1$–C$_4$ alkyl and the other R represents a substituent selected from the group consisting of C$_1$–C$_4$ alkyl and H, and (II) the water-soluble salts thereof, and a coupler therefor, said developer and said coupler being present in the molar range of 2:1 to 1:2.

2. The dyestuff according to claim 1 wherein the developer is 4,7-diamino-5-methylindazole.

3. The dyestuff according to claim 1 wherein the developer is 4,7-diamino-5,6-dimethylindazole.

4. The dyestuff according to claim 1 wherein the developer is a sulfate salt of said substituted 4,7-diaminoindazole.

5. The dyestuff according to claim 1 wherein the coupler is guaiacol.

6. The dyestuff according to claim 1 wherein the coupler is 1-phenyl-3-amino-5-pyrazolone.

TABLE 2

| | Hair Dyed with 5,6-Diaminoindazole + Coupler Combinations | | | | |
|---|---|---|---|---|---|
| | | Oxidizing Agent | | | |
| | | H$_2$O$_2$ | | | NaIO$_4$ | |
| Run No. | Coupler | Aqueous (pH 10.7) | Cream (pH 10.3) | Air | Aqueous (pH 10.6) | Cream (pH 10.4) |
| 1 | α-Naphthol | Brownish grey | Brownish grey | Not dyed | Greyish brown | Greyish brown |
| 2 | m-Aminophenol | Orange grey | Orange grey | " | Greyish beige | Brownish grey |
| 3 | 2,4-Diaminoanisole | Brownish grey | Brownish grey | " | Brownish grey | Brownish grey |
| 4 | 5,6-Diaminoindazole | Brownish grey | Brownish grey | " | Brownish grey | Yellowish grey |

TABLE 3

| | Hair Dyed with 6-Aminoindazole + Coupler Combinations | | | |
|---|---|---|---|---|
| Run No. | Coupler | Oxidizing Agent H$_2$O$_2$ | Air | NaIO$_4$ |
| 1 | α-Naphthol | Brownish orange | Not dyed | Brownish orange |
| 2 | m-Aminophenol | Not dyed | " | Olive brown |
| 3 | 2,4-Diaminoanisole | Brownish grey | Greyish beige | Brown |
| 4 | 6-Aminoindazole | Auburn | Not dyed | Brownish orange |

I claim:

1. A hair dyestuff of the developer-coupler type, wherein the developer is selected from the group consisting of (I) a substituted 4,7-diaminoindazole of the formula:

7. The dyestuff according to claim 1 wherein the coupler is α-naphthol.

8. The dyestuff according to claim 1 wherein the coupler is 2,4-diaminoanisole.

9. The dyestuff according to claim 1 wherein the coupler is m-toluenediamine.

10. The dyestuff according to claim 1 wherein the developer and coupler are present in substantially equimolecular proportions.

11. A preparation suitable for the dyeing of human hair, consisting essentially of:
(1) 0.2% to 5% by weight of the hair dyestuff according to claim 1;
(2) 0.5% to 30% by weight of a non-cationic surfactant;
(3) 0.1% to 25% by weight of a thickener;
(4) 0% to 5% by weight of a direct dye for hair;
(5) 0% to 5% by weight of an oxidizing agent; and
(6) water.

12. The preparation according to claim 11 having a pH in the range of 8–10.

13. The preparation according to claim 11 wherein the thickener is a hydrophobic fatty material and the preparation is an emulsion of cream viscosity.

14. The preparation according to claim 11 wherein the developer is 4,7-diamino-5-methylindazole and the coupler is guaiacol.

15. The preparation according to claim 11 wherein the developer is 4,7-diamino-5,6-dimethylindazole.

16. The preparation according to claim 12 wherein said surfactant is the sodium salt of the half ester of $C_{12}$–$C_{18}$ fatty alcohols with sulfuric acid.

17. The preparation according to claim 11 wherein the preparation contains nitro-p-phenylenediamine as a direct dye.

18. The preparation according to claim 11 wherein the oxidizing agent is hydrogen peroxide.

19. A process for the dyeing of human hair, which comprises contacting said hair with an effective amount of the preparation according to claim 11 at a temperature between 15° C and 40° C. with access of air until at least part of the dyestuff in said preparation has oxidized, and washing said hair to remove the residue of said preparation.

20. The process according to claim 19 wherein the preparation has an alkaline pH.

21. The process according to claim 19 wherein oxidation of said dyestuff is effected only by the action of air.

* * * * *